United States Patent
Palmer

(10) Patent No.: US 7,110,822 B1
(45) Date of Patent: Sep. 19, 2006

(54) REMOTE STATUS AND CONTROL DEVICE FOR A COCHLEAR IMPLANT SYSTEM

(75) Inventor: Logan P Palmer, Santa Monica, CA (US)

(73) Assignee: Advanced Bionics Corporation, Valencia, CA (US)

(*) Notice: Subject to any disclaimer, the term of this patent is extended or adjusted under 35 U.S.C. 154(b) by 513 days.

(21) Appl. No.: 10/418,984

(22) Filed: Apr. 18, 2003

Related U.S. Application Data

(60) Provisional application No. 60/375,183, filed on Apr. 23, 2002.

(51) Int. Cl.
*A61N 1/08* (2006.01)

(52) U.S. Cl. .......................................... 607/57; 607/55

(58) Field of Classification Search ............. 607/55–57
See application file for complete search history.

(56) References Cited

U.S. PATENT DOCUMENTS

| | | | |
|---|---|---|---|
| 4,532,930 A | 8/1985 | Crosby et al. | |
| 5,314,453 A | 5/1994 | Jeutter | |
| 5,344,387 A | 9/1994 | Lupin | |
| 5,571,148 A * | 11/1996 | Loeb et al. | 607/57 |
| 5,584,869 A | 12/1996 | Heck et al. | |
| 5,603,726 A | 2/1997 | Schulman et al. | |
| 5,824,022 A * | 10/1998 | Zilberman et al. | 607/57 |
| 6,005,955 A | 12/1999 | Kroll et al. | |
| 6,157,861 A | 12/2000 | Faltys et al. | |
| 6,195,585 B1 * | 2/2001 | Karunasiri et al. | 607/57 |
| 6,219,580 B1 * | 4/2001 | Faltys et al. | 607/57 |
| 6,334,072 B1 * | 12/2001 | Leysieffer | 607/57 |
| 6,394,947 B1 * | 5/2002 | Leysieffer | 600/25 |
| 6,415,186 B1 * | 7/2002 | Chim et al. | 607/57 |

* cited by examiner

*Primary Examiner*—Robert E. Pezzuto
*Assistant Examiner*—Brian T. Gedeon
(74) *Attorney, Agent, or Firm*—Bryant R. Gold; Victoria A. Poissant

(57) ABSTRACT

A hand-held remote unit functions as both a remote status device and a control device for a cochlear implant system. When placed near the headpiece of a cochlear implant system, the remote unit monitors the forward telemetry signal transmitted between an external speech processor, e.g., a behind-the-ear (BTE) speech processor, and an implanted unit, thereby providing the remote unit with the ability to output status information regarding the system. The remote unit may also generate a back telemetry signal that when properly received by the speech processor causes a forward telemetry signal to be generated that controls the implant unit.

15 Claims, 3 Drawing Sheets

REMOTE STATUS AND CONTROL DEVICE FOR A COCHLEAR IMPLANT SYSTEM

The present application claims the benefit of U.S. Provisional Application Ser. No. 60/375,183, filed Apr. 23, 2002, which application is incorporated herein by reference.

BACKGROUND OF THE INVENTION

The present invention relates to cochlear implant systems, and more particularly to a device that may be used with a cochlear implant system to provide an external indication of the status of the system and to provide limited control of the system.

Remote control devices, including status indicators, for use with cochlear implant systems are known in the art. See, e.g., U.S. Pat. Nos. 5,584,869 and 5,824,022, incorporated herein by reference.

Sometimes, the status-indicating function of the external device has a very limited function, e.g., to indicate proper alignment between an external coil and an implanted coil so that maximum power transfer may occur, as taught, e.g., in U.S. Pat. No. 5,314,453.

It is desirable to monitor the operation of a cochlear implant system from outside of the system to determine whether the system is functioning correctly, and to monitor the settings for such parameters as volume, sensitivity, and program selection. Such external monitoring is particularly important in the case of pediatric implantees, and with behind-the-ear (BTE) packaging for the external speech processor, where there is limited space for controls and indicators on the device. In addition, it is also desirable to be able to control the operation of the cochlear implant from a remote device, again due to limited controls and indicators available in a BTE package.

SUMMARY OF THE INVENTION

The present invention addresses the above and other needs by providing a hand-held remote device (hereafter referred to as the "Remote") that, when placed near the headpiece of the cochlear implant system, can monitor the forward-telemetry (FT) signal between the external speech processor and the implanted stimulator. This provides a means by which the speech processor can output status information that the Remote receives and displays. Also, the Remote includes circuitry that allows it to transmit back-telemetry (BT) data at the request of the speech processor, which allows the Remote to input control information to the system.

In one embodiment, the invention may be characterized as a remote device adapted for use with a cochlear implant system. The cochlear implant system includes an implant device adapted to receive forward telemetry signals from an external speech processor. The remote device comprises: (a) a forward telemetry receiver that receives the forward telemetry signals transmitted from the external speech processor; (b) means for detecting status information contained within the forward telemetry signal; and (c) means for displaying the status information detected within the forward telemetry signal. Thus, the remote device functions as a remote status device that allows a user of the cochlear implant system to receive status information regarding operation of the cochlear implant system.

In another embodiment, the invention may be characterized as a remote status indicating device for use with an existing cochlear implant system. Such cochlear implant system includes an implant device and an external speech processor. In operation, the speech processor generates forward telemetry signals that are received by the implant device and that control the operation of the implant device. The remote status indicating device in accordance with this characterization of the invention includes the following components: (a) a forward telemetry receiving coil adapted to sense forward telemetry signals; (b) a forward telemetry detector circuit coupled to the forward telemetry receiving coil, and wherein the forward telemetry detector circuit generates a serial data stream representative of information contained within the forward telemetry signals and a forward telemetry bit clock signal representative of bit times between individual data bits contained with the serial data stream; (c) a word framing circuit responsive to the serial data stream and bit clock signal that generates parallel data streams and a word clock signal; (d) command framing circuitry that frames command information contained within the forward telemetry signals; (e) processing means responsive to the command framing for generating informational status signals indicative of selected command information contained within the forward telemetry signals; (f) a display coupled to the processing means, wherein the display is adapted to display the status information contained within the status signals generated by the processing means; and (g) user-selectable controls coupled to the processing means for allowing a user to select which command information is to be included within the displayed status information.

Yet another embodiment, in addition to all the components identified in the preceding paragraph, further includes: (h) a back telemetry carrier synthesizer that generates a back telemetry carrier signal; (i) a back telemetry coil; (j) a back telemetry transmitter circuit that receives the back telemetry carrier signal and that modulates the back telemetry carrier signal with control data received from the processing means, and that further applies the modulated back telemetry carrier signal to the back telemetry coil; (k) wherein the control data that modulates the back telemetry carrier signal comprises at least in part user-selectable control data; and (l) means for synchronizing the modulated back telemetry data with back telemetry data so that it can be received by the external speech processor; (m) wherein the external speech processor in response to receipt of the back telemetry data from the remote status indicating device generates control data that is transmitted to the implant device, whereby the remote status indicating device further functions as a remote control device.

Still another embodiment of the invention may be characterized as a cochlear implant system that includes: (a) a behind-the ear (BTE) external speech processor adapted to generate forward telemetry signals containing control information; (b) an implant device adapted to receive the forward telemetry signals from the BTE speech processor; and (c) a remote unit adapted to provide status information relative to the operation of the implant system. The remote unit of such embodiment includes: a forward telemetry receiver that receives the forward telemetry signals transmitted from the external BTE speech processor, means for detecting status information contained within the forward telemetry signal, and means for displaying the status information detected within the forward telemetry signal.

BRIEF DESCRIPTION OF THE DRAWINGS

The present invention will be better understood with reference to the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The details associated with the operation of a typical cochlear implant system may be found in one or more of the following U.S. patents, each of which is incorporated herein by reference: U.S. Pat. Nos. 6,157,861; 6,002,966; 5,824,022; 5,603,726; 5,344,387; 4,532,930.

Figure 1:
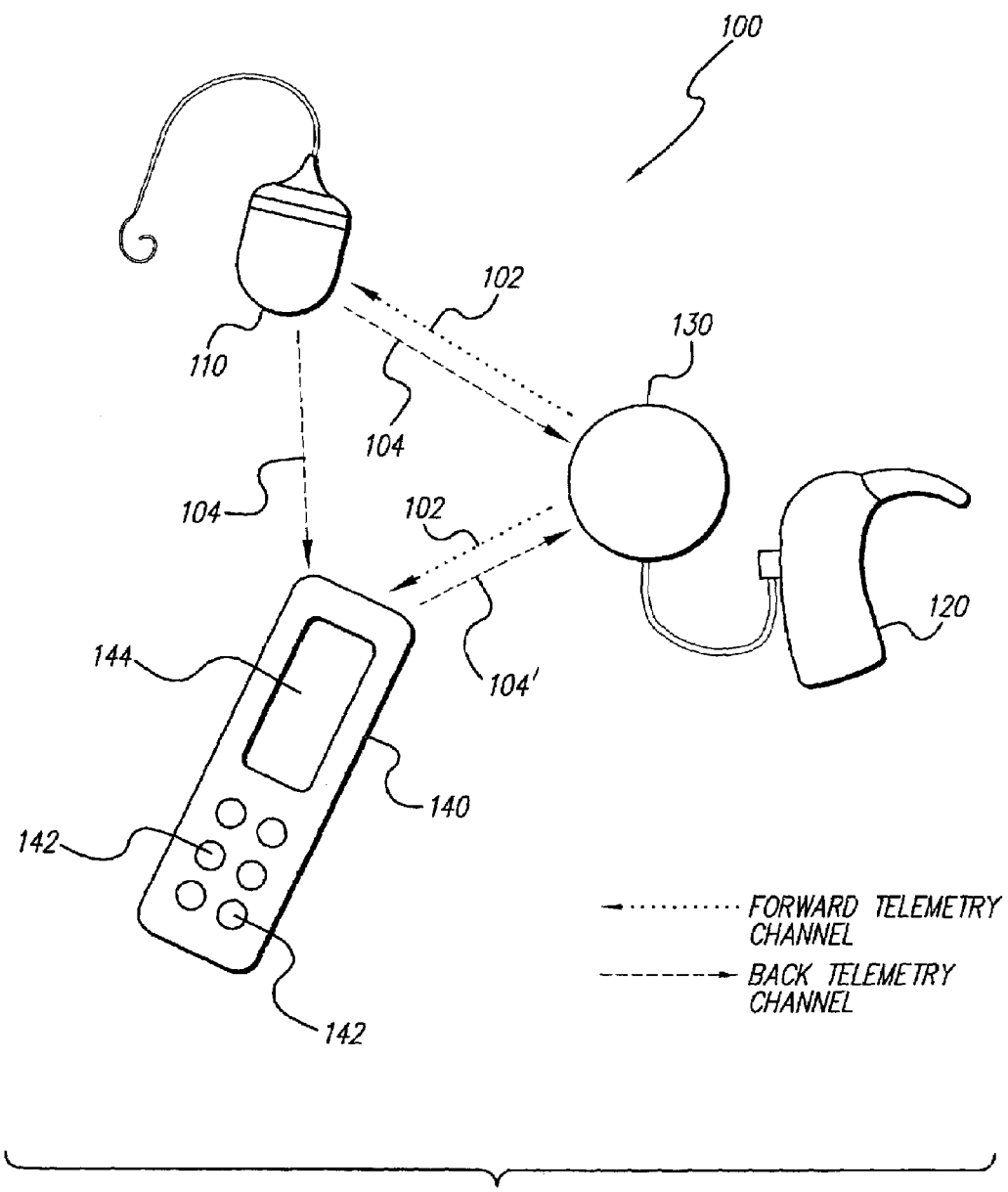
FIG. 1 is a pictorial diagram showing the various components of a cochlear implant system and how the Remote of the present invention is used in conjunction with the other elements of the cochlear implant system.

Turning first to FIG. 1, there is shown a pictorial diagram showing how the Remote of the present invention is used in conjunction with a cochlear implant system 100. The cochlear implant system 100 comprises on an external speech processor 120, an implanted device ("implant") 110, and a headpiece 130. The speech processor 120 contains a programmable digital signal processor (DSP) that controls the overall operation of the system. The speech processor communicates with the implant 110 through inductively-coupled radio-frequency (RF) channels that operate between coils in the headpiece 130 and the implant 110. The forward-telemetry channel, illustrated in FIG. 1 as the dotted line 102, is used to transmit power and data into the implant 110; the back-telemetry channel, illustrated in FIG. 1 as the dashed line 104, communicates data from the implant 110 to speech processor 120 through the headpiece 130.

A remote device 140 (referred to herein as the "Remote" 140), made in accordance with the present invention, when brought near the headpiece 130, monitors the forward-telemetry signal 102 emanating from the headpiece, and thus receives status information from the speech processor 120. This capability alone provides a status-only Remote.

Additionally, the Remote 140, when needed, may monitor the back telemetry signal 104 emanating from the implant 110, thereby allowing it to directly monitor the status of the implant 110.

The Remote 140 also includes transmission circuitry that gives it the ability to transmit a back telemetry signal 104' to the headpiece 130, which signal 104' is then coupled into the speech processor 120. This back telemetry signal 104' is generated independent of the signal 104, although the signal 104, generated by the implant unit 110, may be received and used to determine the proper bit framing (phase) to include in the signal 104'. Typically, the signal 104' will be generated as a function of user-selected controls, e.g., buttons 142, included on the Remote. This ability, as explained in greater detail below, gives the Remote 140 the ability to control the implant system.

Advantageously, the only changes to the cochlear implant system 100 needed to support operation of the Remote 140 are to the speech processor 120. Moreover, such changes need only be made to the software of the speech processor 120. Thus, the Remote 140 provided by the present invention may be used with existing cochlear implants 110 and, with only a software modification, existing speech processors 120.

Figure 2:
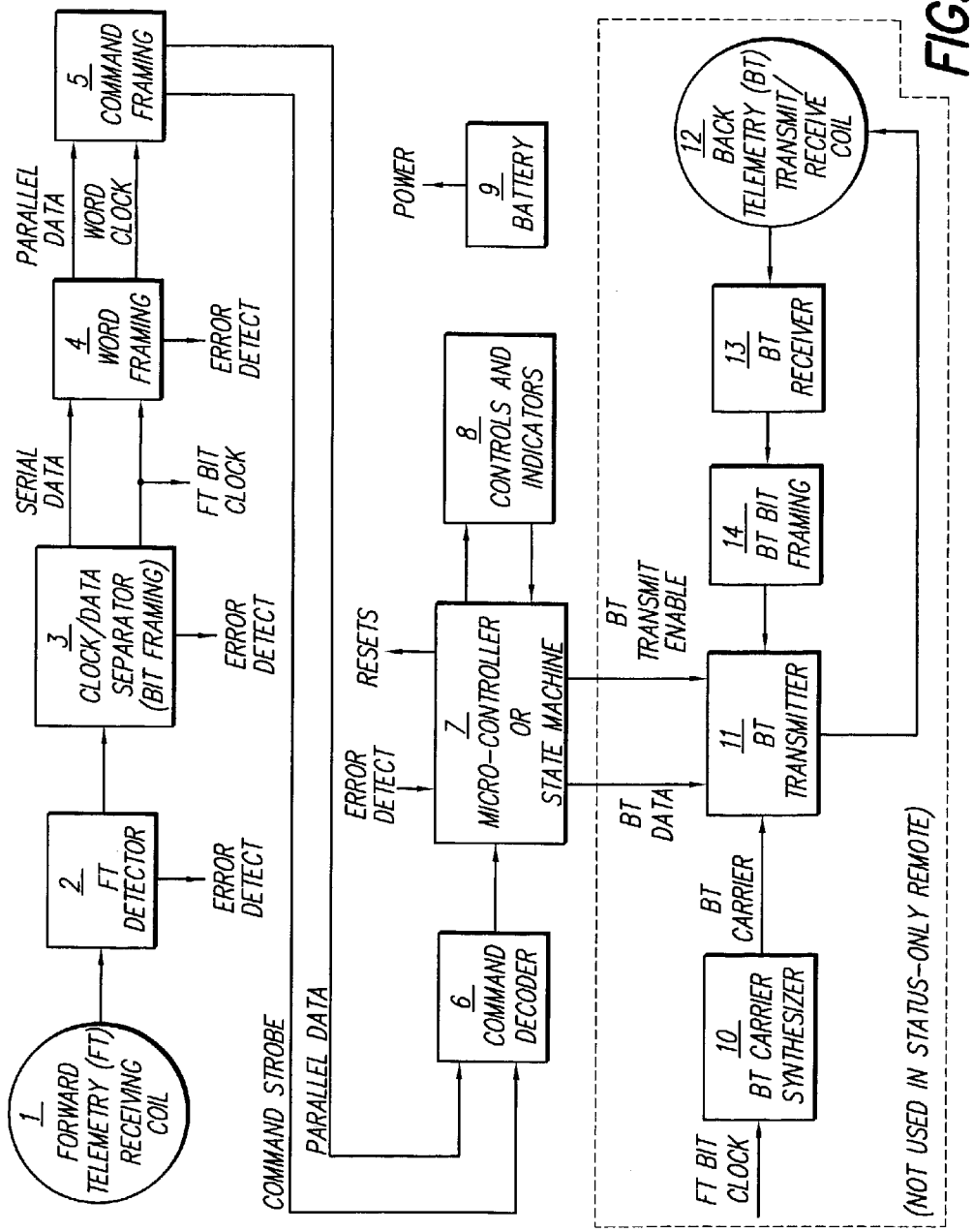
FIG. 2 shows a block diagram of a Remote made in accordance with the present invention.

Turning next to FIG. 2, a block diagram of the Remote 140 is illustrated. As seen in FIG. 2, the Remote includes the following parts:

1) Forward Telemetry (FT) Receiving Coil: The FT receiving coil 1, when held near the system headpiece 130, couples inductively with the headpiece coil, and intercepts the radio-frequency (RF) FT signal that is being transmitted by the speech processor 120.

2) FT Detector: This circuit demodulates the forward telemetry (FT) signal 102 from the coil and outputs a serial digital data stream. The detector and receiving coil present a relatively high impedance to the headpiece coil, and so draw minimal energy from the system, thus minimizing any power loss to the implant. This FT Detector circuit 2 also detects the absence of any RF signal, which absence of an RF signal is interpreted as an error condition, and causes a reset signal to be generated and sent to the rest of the Remote 140.

3) Clock/Data Separator (Bit Framing): This circuit receives the serial data stream from the FT Detector 2, which typically uses a frequency-modulation (FM) encoding scheme, whereby clock and data information are both embedded in the stream. This clock/data separator circuit 3 outputs separate clock and data signals. The data is typically formatted in a serial non-return-to-zero (NRZ) format, although other formats could also be used. An important aspect of this circuit is that it must establish the bit boundaries without going through a FT initialization sequence, which FT initialization sequence is used to establish communication between the speech processor and the implant. This establishment of the bit boundaries is accomplished by means of mono-stable multivibrators (one-shots), in combination with a phase-locked loop (PLL) circuit. The clock/data separator circuit 3 also detects errors in the incoming FM encoding format, with such errors causing a reset signal to be generated and sent to the Remote 140.

Figure 3:
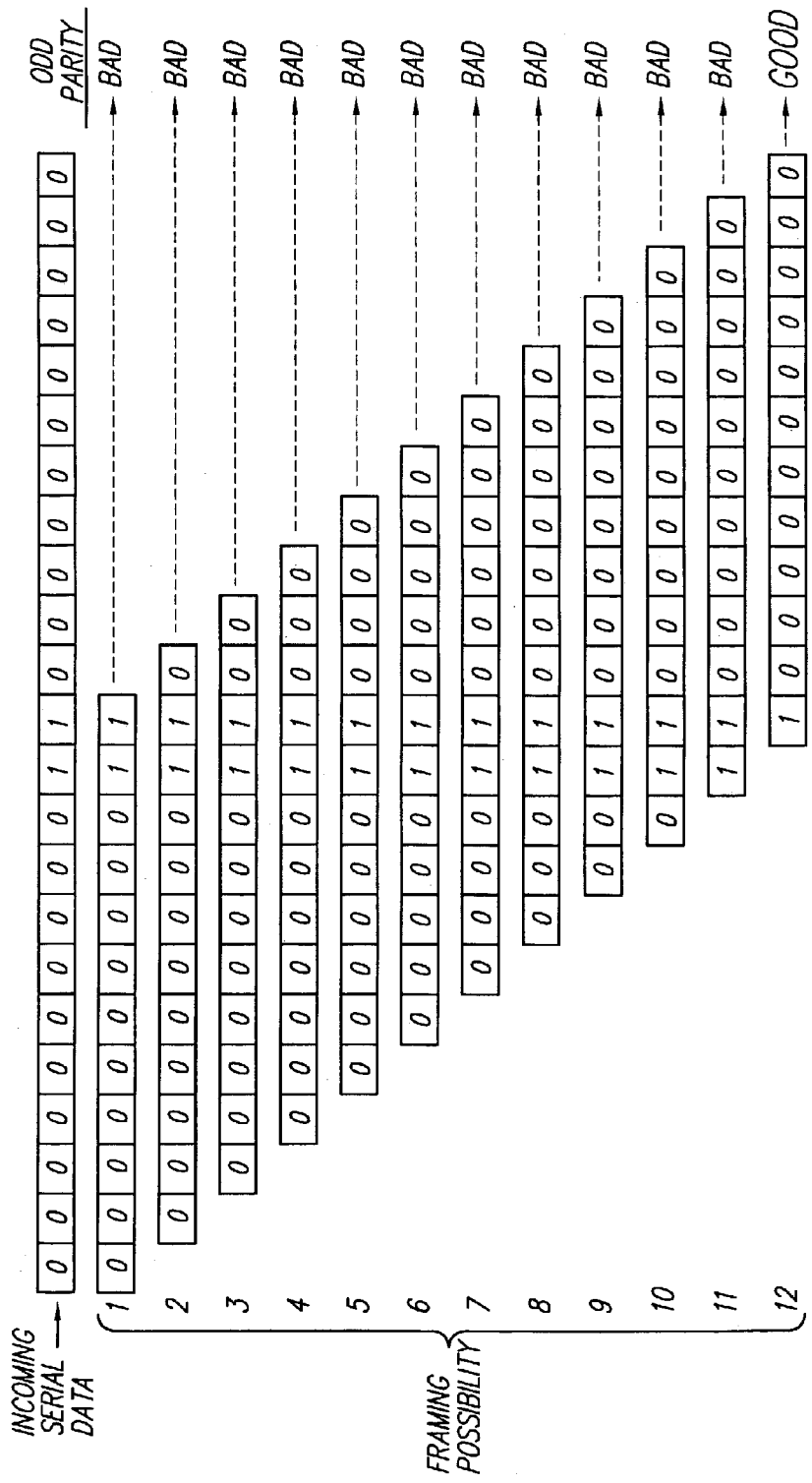
FIG. 3 illustrates the word framing "scoreboarding" technique employed by the present invention.

4) Word Framing: This circuit 4 receives the separated NRZ serial data and clock signals, and establishes the word boundaries. Again, because the remote does not take part in the normal forward telemetry (FT) initialization sequence, a special method is required. One such method is to take advantage of the word-level parity by means of a "scoreboarding" technique. For example, if the FT protocol uses 12-bit words with odd parity, the word framing circuit would continually examine all 12 possible ways that the words could be framed, and check parity for each possibility. When a parity error is detected, it is posted in the "scoreboard" for that framing possibility. Eventually all but the correct framing possibility will post errors, and so the process continues until only one possibility has not posted an error. This remaining possibility is therefore the correct framing. This "scoreboarding" process is illustrated in FIG. 3. Once framing is established, the word framing circuit outputs parallel data and word clock signals. On the other hand, if all 12 framing possibilities detect errors, this indicates either a receive data error or an error in the FT initialization sequence. Such error condition generated an error detect signal that resets the Remote 140.

It should be noted that in the event the word framing circuitry takes too long to converge on correct framing due to the received data pattern, then the speech processor can periodically output a sequence of "no-op" words that are ignored by the implant 110 but can only be framed one way with good parity, e.g., 0x001 (hexadecimal) followed by 0x800, or vice-versa.

5) Command Framing: If the FT protocol supports multi-word commands, command framing circuitry 5 is necessary to determine command boundaries. For example, in the C-II cochlear implant system available from Advanced Bionics Corporation, of Sylmar, Calif., a word where bit 11 ("Amplitude") and bit 10 ("Continue") are both 0 marks the end of a command. Upon receipt of such a word, the command decoding circuit 5 can start with the next non-amplitude word. The decoding circuit 5 passes the parallel data words through and outputs a command strobe, which indicates the start of each command.

6) Command Decoder: The command decoder circuit 6 receives FT commands and responds to a special subset of the command protocol that is not used by the implant. The speech processor 120 will periodically send out a sequence of commands that are ignored by the implant but are recognized by the Remote 140, if present. For example, in the C-II command protocol used in Advanced Bionics' C-II cochlear implant system, there are 64 possible register addresses, but only 34 are used by the implant. Thus, the speech processor 120 may communicate to the Remote 140 by sending write commands to registers that are present only in the Remote 140. The speech processor 120 sends such commands on a periodic basis (typically a few times per second). Moreover, whenever the Remote 140 is brought near the headpiece 130, the Remote 140 will intercept these commands and respond as required.

7) Microcontroller or State Machine (MCU/SM): This circuit 7 receives the decoded commands from the command decoder circuit 6. From these decoded commands it extracts the status information sent by the speech processor 120 for display on the visual indicators 144 included as part of the Remote 140. This circuit 7 also receives input from the user-activated controls, e.g., buttons or switches 142, of the Remote 140 to determine the state of the status display and control information to be sent to the speech processor 120. This circuit controls the overall operation of the Remote 140, receives error information from the various detector/framing blocks, and generates reset signals for the rest of the Remote 140.

8) Controls and Indicators: The Remote 140 includes various controls 142 and a display 144. The controls 142 consist of user input mechanisms (switches, knobs, push-buttons, etc.) and the display 144 comprises any suitable display device, or an array of display devices (LEDs, LCDs, etc.) that form the user interface for the Remote 144. Through the display 144 the user can view status, select the type of status information to be displayed, and send command(s) to the speech processor 120.

9) Battery: A battery 9 is included in the Remote 140 to power all of the electronics. The battery may be either a primary battery or a rechargeable battery. The battery may be replaced, as required. (Even a rechargeable battery may need to be replaced after a specified number of recharges.)

NOTE: Blocks 10) through 14) in FIG. 2, described next, are necessary only for a bi-directional version of the Remote 140. If the Remote 140 is implemented as a status-only device, these blocks need not be included, or (if included) need not be activated.

10) Back-Telemetry (BT) Carrier Synthesizer: The BT Carrier Synthesizer circuit 10 generates the carrier frequency for transmission of information to the speech processor, using the back-telemetry channel. One embodiment of the BT Carrier Synthesizer circuit comprises a phase-locked-loop (PLL)-based synthesizer circuit that uses the FT bit clock as a reference frequency.

11) BT Transmitter: The BT Transmitter circuit 11 sends control information to the speech processor 120, using the same frequency and protocol as are used by the implant 110. The BT Transmitter circuit 11 is enabled by the MicroController or State Machine (MCU/SM) 7, described above, which also supplies the data to be transmitted. The MCU/SM 7, in turn, only enables the BT Transmitter when requested to do so by the speech processor 120, which also controls the BT transmitter in the implant. In this manner, the speech processor 120 ensures that there are no collisions between BT transmissions from the implant 110 and the Remote 140. It should be noted that a control sequence from the user interface of the Remote 140 does not result in an immediate BT transmission. Rather, the MCU/SM 7 will first store the control sequence and will then wait until it is requested to send data by the speech processor 120.

12) BT Transmit/Receive Coil: The BT transmit/receive coil 12 is located adjacent to the FT coil 1, and as such is also coupled with a headpiece coil and the BT transmit coil in the implant. Alternatively, the FT coil 1 may be shared with the BT channel with the addition of an appropriate matching network.

13) BT Receiver: The BT Receiver circuit 13 receives and demodulates the back-telemetry RF signal that is transmitted from the implant 110. A serial digital data stream is output by the implant.

14) BT Bit Framing: The BT Framing circuit 14 monitors the BT serial data stream from the BT Receiver when the implant is transmitting, and detects the phase of the bit transitions relative to an internal counter. This circuit is used to control the bit boundary times (phase) of the Remote's BT transmissions so that it matches that of the implant, and so that the speech processor can correctly demodulate and decode BT data from the Remote.

NOTE: As an alternative to using a BT Receiver within the Remote 140, one embodiment may have the speech processor send commands that control the BT bit phase in the Remote. The correct phasing would be found by trial and error, under control of the speech processor 120. The disadvantage of this alternative approach is that it would take longer to establish the BT communication link between the Remote 140 and speech processor 120.

As described above, it is seen that the present invention provides a hand-held remote unit 140 that, when placed near the headpiece of a cochlear implant system 100, may monitor the forward telemetry (FT) signal transmitted between the external speech processor 120 and the implant unit 110, thereby providing the Remote unit 140 with the ability to output status information regarding the system; and which (in some embodiments) may also generate a back telemetry (BT) signal that when received by the speech processor causes a FT signal to be generated that controls the implant unit 110. Hence, in this manner, the Remote unit 140 functions as both a remote status device and a control device for a cochlear implant system.

While the invention herein disclosed has been described by means of specific embodiments and applications thereof, numerous modifications and variations could be made thereto by those skilled in the art without departing from the scope of the invention set forth in the claims.

What is claimed is:

1. A remote device adapted for use with a cochlear implant system, said cochlear implant system including an implant device adapted to receive forward telemetry signals emanating from a headpiece of an external speech processor, said remote device comprising:

a forward telemetry receiver that monitors the forward-telemetry signal emanating from the headpiece of the external speech processor;

means for detecting status information contained within the forward telemetry signal; and means for displaying the status information detected within the forward telemetry signal;

wherein the remote device functions as a remote status device that allows a user of the cochlear implant system to receive status information regarding operation of the cochlear implant system wherein said forward telemetry signals simultaneously emanate from the headpiece of the external processor.

2. The remote device of claim 1 wherein said implant device is further adapted to generate a back telemetry signal in response to a request from the external speech processor, and wherein said remote device further includes:

means for monitoring the back telemetry signal emanating from the implant device;

control means for modulating the back telemetry signal with user-selected information so as to create another back telemetry signal independent of the back telemetry signal emanating from the implant device;

wherein the external speech processor receives the other back telemetry signal and sends control information to the implant device in response thereto, whereby the user-selected information is included in the control information sent to the implant device, whereby the remote device also functions as a remote control device that allows a user of the cochlear implant system to send user-selected control information to the implant device.

3. The remote device of claim 2 wherein the means for generating and transmitting a back telemetry signal comprises a back telemetry carrier synthesizer;

a back telemetry transmitter circuit coupled to the back telemetry carrier synthesizer; and a back telemetry transmit coil coupled to the back telemetry transmitter circuit through which the back telemetry signal is transmitted.

4. The remote device of claim 3 wherein the control means for modulating the back telemetry signal with user-selectable information comprises:

a microcontroller or state machine that generates back telemetry data;

user-selectable controls for generating control signals for use by the microcontroller or state machine that determine, in part, the type of back telemetry data generated by the microcontroller or state machine; and means for applying the back-telemetry data to the back telemetry transmitter circuit, whereby the back telemetry data modulates the back telemetry signal.

5. The remote device of claim 4 wherein the user selectable controls are selected from the group comprising switches, knobs, and pushbuttons.

6. A remote status indicating device for use with an existing cochlear implant system, the cochlear implant system including an implant device and an external speech processor, and wherein the speech processor generates forward telemetry signals that emanate from the speech processor and are received by the implant device and that control the operation of the implant device, the remote status indicating device comprising:

a forward telemetry receiving coil adapted to sense and monitor the forward telemetry signals emanating from the speech processor;

a forward telemetry detector circuit coupled to the forward telemetry receiving coil, wherein the forward telemetry detector circuit generates a serial data stream representative of information contained within the forward telemetry signals and a forward telemetry bit clock signal representative of bit times between individual data bits contained with the serial data stream;

a word framing circuit responsive to the serial data stream and bit clock signal that generates parallel data streams and a word clock signal;

command framing circuitry that frames command information contained within the forward telemetry signals;

processing means responsive to the command framing for generating informational status signals indicative of selected command information contained within the forward telemetry signals;

a display coupled to the processing means, wherein the display is adapted to display the status information contained within the status signals generated by the processing means; and user-selectable controls coupled to the processing means for allowing a user to select which command information is to be included within the displayed status information wherein said forward telemetry signals simultaneously emanate from the headpiece of the external processor.

7. The remote status indicating device of claim 6 further including:

a back telemetry carrier synthesizer that generates a back telemetry carrier signal;

a back telemetry coil;

a back telemetry transmitter circuit that receives the back telemetry carrier signal and that modulates the back telemetry carrier signal with control data received from the processing means, and that further applies the modulated back telemetry carrier signal to the back telemetry coil;

wherein the control data that modulates the back telemetry carrier signal comprises at least in part user-selectable control data; and means for synchronizing the modulated back telemetry data with back telemetry data so that it can be received by the external speech processor;

wherein the external speech processor in response to receipt of the back telemetry data from the remote status indicating device generates control data that is transmitted to the implant device, whereby the remote status indicating device further functions as a remote control device.

8. The remote status indicating device of claim 7 wherein the means for synchronizing the modulated back telemetry data so that it can be received by the external speech processor comprises:

means for receiving back telemetry data from the implant device;

means for extracting back telemetry bit framing data from the back telemetry data received from the implant device; and means for applying the extracted back telemetry bit framing data to the back telemetry transmitter circuit.

9. A cochlear implant system comprising:
a behind-the ear (BTE) external speech processor adapted to generate forward telemetry signals containing control information that emanate from the BTE external speech processor;
an implant device adapted to receive the forward telemetry signals that emanate from the BTE speech processor;
a remote unit adapted to provide status information relative to the operation of the implant system, the remote unit comprising:
 a forward telemetry receiver that receives and monitors the forward telemetry signals emanating from the external BTE speech processor,
 means for detecting status information contained within the monitored forward telemetry signal, and
 means for displaying the status information detected within the monitored forward telemetry signal wherein said forward telemetry signals simultaneously emanate from the headpiece of the external processor.

10. The cochlear implant system of claim 9 wherein said implant device further includes means for generating a back telemetry signal in response to a request from the external BTE speech processor; and
wherein said remote unit further includes:
 means for generating and transmitting a second back telemetry signal,
 control means for modulating the second back telemetry signal with user-selected information,
 wherein the external BTE speech processor receives the second back telemetry signal and sends control information to the implant device in response thereto, whereby the user-selected information is included in the control information sent to the implant device, whereby the remote unit also functions as a remote control unit that allows a user of the cochlear implant system to send user-selected control information to the implant device.

11. A cochlear implant system comprising:
a behind-the ear (BTE) external speech processor adapted to generate forward telemetry signals containing control information;
an implant device adapted to receive the forward telemetry signals from the BTE speech processor, wherein said implant device further includes means for generating a back telemetry signal in response to a request from the external BTE speech processor;
a remote unit adapted to provide status information relative to the operation of the implant system, the remote unit comprising:
 a forward telemetry receiver that receives the forward telemetry signals transmitted from the external BTE speech processor,
 means for detecting status information contained within the forward telemetry signal,
 means for displaying the status information detected within the forward telemetry signal,
 means for generating and transmitting a second back telemetry signal,
 control means for modulating the second back telemetry signal with user-selected information,
 wherein the external BTE speech processor receives the second back telemetry signal and sends control information to the implant device in response thereto, whereby the user-selected information is included in the control information sent to the implant device, whereby the remote unit also functions as a remote control unit that allows a user of the cochlear implant system to send user-selected control information to the implant device.

12. The cochlear implant system of claim 11 wherein the control means are selected from the group comprising switches, knobs, and pushbuttons.

13. A remote status indicating device for use with an existing cochlear implant system, the cochlear implant system including an implant device and an external speech processor, and wherein the speech processor generates forward telemetry signals that are received by the implant device and that control the operation of the implant device, the remote status indicating device comprising:
 a forward telemetry receiving coil adapted to sense forward telemetry signals;
 a forward telemetry detector circuit coupled to the forward telemetry receiving coil, wherein the forward telemetry detector circuit generates a serial data stream representative of information contained within the forward telemetry signals and a forward telemetry bit clock signal representative of bit times between individual data bits contained with the serial data stream;
 a word framing circuit responsive to the serial data stream and bit clock signal that generates parallel data streams and a word clock signal;
 command framing circuitry that frames command information contained within the forward telemetry signals;
 processing means responsive to the command framing for generating informational status signals indicative of selected command information contained within the forward telemetry signals;
 a display coupled to the processing means, wherein the display is adapted to display the status information contained within the status signals generated by the processing means;
 user-selectable controls coupled to the processing means for allowing a user to select which command information is to be included within the displayed status information;
 a back telemetry carrier synthesizer that generates a back telemetry carrier signal;
 a back telemetry coil;
 a back telemetry transmitter circuit that receives the back telemetry carrier signal and that modulates the back telemetry carrier signal with control data received from the processing means, and that further applies the modulated back telemetry carrier signal to the back telemetry coil;
 wherein the control data that modulates the back telemetry carrier signal comprises at least in part user-selectable control data; and
 means for synchronizing the modulated back telemetry data with back telemetry data so that it can be received by the external speech processor;
 wherein the external speech processor in response to receipt of the back telemetry data from the remote status indicating device generates control data that is transmitted to the implant device, whereby the remote status indicating device further functions as a remote control device.

14. The remote status indicating device of claim 13 wherein the means for synchronizing the modulated back telemetry data so that it can be received by the external speech processor comprises:
 means for receiving back telemetry data from the implant device;

means for extracting back telemetry bit framing data from the back telemetry data received from the implant device; and means for applying the extracted back telemetry bit framing data to the back telemetry transmitter circuit.

15. The remote status indicating device of claim 13 wherein the user-selectable controls are selected from the group comprising switches, knobs, and pushbuttons.

* * * * *